US012354190B2

United States Patent
Ye et al.

(10) Patent No.: US 12,354,190 B2
(45) Date of Patent: Jul. 8, 2025

(54) QUANTITATIVE SUSCEPTIBILITY MAPPING IMAGE PROCESSING METHOD USING NEURAL NETWORK BASED ON UNSUPERVISED LEARNING AND APPARATUS THEREFOR

(71) Applicant: Korea Advanced Institute of Science and Technology, Daejeon (KR)

(72) Inventors: JongChul Ye, Daejeon (KR); Gyutaek Oh, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 555 days.

(21) Appl. No.: 17/711,944

(22) Filed: Apr. 1, 2022

(65) Prior Publication Data
US 2022/0358691 A1    Nov. 10, 2022

(30) Foreign Application Priority Data

Apr. 2, 2021 (KR) .................. 10-2021-0043432
Feb. 10, 2022 (KR) .................. 10-2022-0017320

(51) Int. Cl.
| G06T 11/00 | (2006.01) |
| A61B 5/055 | (2006.01) |
| G01R 33/44 | (2006.01) |
| G01R 33/56 | (2006.01) |
| G06N 3/08 | (2023.01) |

(52) U.S. Cl.
CPC ............. *G06T 11/006* (2013.01); *A61B 5/055* (2013.01); *G01R 33/443* (2013.01); *G01R 33/5608* (2013.01); *G06N 3/08* (2013.01)

(58) Field of Classification Search
CPC ......... G06T 11/006; G06T 2207/10032; G06T 5/00; A61B 5/055; G01R 33/443; G01R 33/5608; G01R 33/56536; G06N 3/08; G06N 3/0464; G06N 3/048; G06N 3/045; G06N 3/047; G06N 3/0475; G06N 3/088; G06N 3/094; G06N 3/044; G06V 10/774; G06V 10/82; G06F 17/153
See application file for complete search history.

(56) References Cited

PUBLICATIONS

"Juan Liu, Deep Learning for Quantitative Susceptibility Mapping Reconstruction, 2020, Marquette University ProQuest Dissertations & Theses, 28091311" (Year: 2020).*

(Continued)

*Primary Examiner* — Chineyere Wills-Burns
*Assistant Examiner* — Phuong Hau Cai
(74) *Attorney, Agent, or Firm* — Christensen O'Connor Johnson Kindness PLLC

(57) ABSTRACT

Disclosed is a quantitative susceptibility mapping image processing method using an unsupervised learning-based neural network and an apparatus therefor. The quantitative susceptibility mapping image processing method includes receiving a phase image and a magnitude image for reconstructing the quantitative susceptibility mapping image, and reconstructing the quantitative susceptibility mapping image corresponding to the received phase image and the received magnitude image using an unsupervised learning-based neural network, and the neural network may be generated based on an optimal transport theory.

12 Claims, 7 Drawing Sheets

(56) References Cited

PUBLICATIONS

"Viraj Shah et. al., Encoding Invariances in Deep Generative Models, Jun. 2019, Machine Learning Image and Video Processing, arXiv—Computer science—Machine Learning" (Year: 2019).*

"Jun-Yan Zhu et. al., Unpaired image-to-image translation using cycle-consistent adversarial networks, 2017, In Computer Vision (ICCV), 2017 IEEE International Conference on, pp. 2223-2232" (Year: 2017).*

"Tim Salimans et al., Improving GANS Using Optimal Transport, 2018, Published as a Conference Paper at ICLR 2018" (Year: 2018).*

"Veronique Fortier et. al., Phase Processing for Quantitative Susceptibility Mapping of Regions with Large Susceptibility and Lack of Signal, Nov. 2017, STIC Scientific and Technical Information Center" (Year: 2017).*

Chunlei Liu et. al., Quantitative Susceptibility Mapping: Contrast Mechanisms and Clinical Applications, Sep. 2015, Tomography, Mar. 2017 (Year: 2015).*

Office Action for Korean patent application No. 10-2022-0017320, mailed Mar. 23, 2025.

Chen, Y., Jakary, A., Avadiappan, S., Hess, C. P., & Lupo, J. M. (2020). QSMGAN: improved quantitative susceptibility mapping using 3D generative adversarial networks with increased receptive field. NeuroImage, 207, 116389.

Lu, G., Zhou, Z., Song, Y., Ren, K., & Yu, Y. (Jul. 2019). Guiding the one-to-one mapping in CycleGAN via optimal transport. In Proceedings of the AAAI conference on artificial intelligence (vol. 33, No. 01, pp. 4432-4439).

* cited by examiner

QUANTITATIVE SUSCEPTIBILITY MAPPING IMAGE PROCESSING METHOD USING NEURAL NETWORK BASED ON UNSUPERVISED LEARNING AND APPARATUS THEREFOR

CROSS-REFERENCE TO RELATED APPLICATIONS

A claim for priority under 35 U.S.C. § 119 is made to Korean Patent Application No. 10-2021-0043432 filed on Apr. 2, 2021 and No. 10-2022-0017320 filed on Feb. 10, 2022, in the Korean Intellectual Property Office, the entire contents of which are hereby incorporated by reference.

BACKGROUND

Embodiments of the inventive concept described herein relate to a quantitative susceptibility mapping image processing technique using an unsupervised learning-based neural network, and more particularly, to a quantitative susceptibility mapping image processing method and apparatus capable of reconstructing the quantitative susceptibility mapping image using the unsupervised learning-based neural network.

Quantitative susceptibility mapping (QSM) is a magnetic resonance imaging (MRI) technique that can quantitatively measure the degree of susceptibility of body tissues in a magnetic field. QSM may provide specific contrast images or provide information that is helpful in diagnosing diseases because QSM is sensitive to biomarkers such as iron deposition.

A quantitative susceptibility mapping image may be obtained from a phase image of a magnetic resonance image. From a mathematical point of view, the phase image of the magnetic resonance image is expressed by the convolution between the quantitative susceptibility mapping image and a dipole kernel. A quantitative susceptibility mapping image may be obtained by dividing a phase image by a dipole kernel in Fourier space, and this process is called dipole inversion. Thus, a magnetic susceptibility distribution can be obtained by deconvolution: for example, dividing the phase by the dipole kernel in the Fourier domain. However, the dipole kernel in the Fourier domain has zeros along the conical surface, which makes the dipole inversion an ill-posed inverse problem.

To overcome these limitations, various dipole inversion approaches have been investigated. Calculation of susceptibility through multiple orientation sampling (COSMOS) is considered as the golden standard algorithm for the dipole inversion. COSMOS restores accurate QSM from multiple head orientation data. However, the acquisition of MR data along multiple head orientations for COSMOS reconstruction takes too much subject's time and effort.

Accordingly, algorithms have been developed for dipole inversion from single head orientation data. For example, filling the area around the conical surface with a threshold value is one of the methods for dipole inversion. Also, the regularization by edge information of the magnitude image can mitigate the ill-posedness of dipole inversion. In addition, dipole inversion algorithms based on compressed sensing have been studied. However, the streaking artifact in the reconstructed QSM and the difficulty of hyperparameter tuning are limitations of the above algorithms.

Recently, deep learning algorithms have also been extensively studied for QSM reconstruction. These algorithms show comparable performance as the classical methods despite the fast computational time. However, most of the existing deep learning methods for QSM reconstruction are based on supervised learning which requires matched pairs of phase images and ground-truth QSM labels. Nonetheless, it has been reported that the reconstructed QSM values are often underestimated.

SUMMARY

Embodiments of the inventive concept provide a quantitative susceptibility mapping image processing method capable of reconstructing a quantitative susceptibility mapping image using an unsupervised learning-based neural network and an apparatus therefor.

According to an exemplary embodiment, a quantitative susceptibility mapping image processing method for reconstructing a quantitative susceptibility mapping (QSM) image includes receiving a phase image and a magnitude image for reconstructing the quantitative susceptibility mapping image, and reconstructing a quantitative susceptibility mapping image corresponding to the received phase image and the received magnitude image using an unsupervised learning-based neural network, wherein the neural network includes a cycle-consistency generative adversarial network (cycleGAN) structure including at least one generator and at least one discriminator to reconstruct the quantitative susceptibility mapping image.

The neural network may be generated based on an optimal transport theory.

The neural network may be trained using a training dataset containing non-matching data.

The neural network may be subjected to unsupervised learning by using a first neural network that generates a first quantitative susceptibility mapping image corresponding to a first phase image and a first magnitude image after receiving the first phase image and the first magnitude image, a first transform unit that performs Fourier transform on the first quantitative susceptibility mapping image, multiplies the first quantitative susceptibility mapping image by a dipole kernel corresponding to the first phase image and the first magnitude image, and performs inverse Fourier transform on the first quantitative susceptibility mapping image to generate a second phase image, a second transform unit that performs Fourier transform on a second quantitative susceptibility mapping image, which is a ground-truth image, and multiplies the second quantitative susceptibility mapping image by a dipole kernel corresponding to the second quantitative susceptibility mapping image, and performs inverse Fourier transform on the second quantitative susceptibility mapping image to generate a third phase image, a second neural network that generates a third quantitative susceptibility mapping image corresponding to the second phase image and a second magnitude image after receiving the second phase image and the second magnitude image, and a third neural network that discriminates the first quantitative susceptibility mapping image and the second quantitative susceptibility mapping image. Here, the first neural network and the second neural network may be the same neural network.

Furthermore, the neural network may be subjected to the unsupervised learning based on a cycle-consistency loss and a gradient difference loss calculated by comparing the first phase image with the second phase image, or the second quantitative susceptibility mapping image with the third quantitative susceptibility mapping image and a total variation loss for the first quantitative susceptibility mapping image, and an adversarial loss between the first quantitative susceptibility mapping image and the second quantitative susceptibility mapping image.

The third neural network may distinguish a quantitative susceptibility mapping image obtained by multiplying the first quantitative susceptibility mapping image by a preset mask and the second quantitative susceptibility mapping image.

The neural network may include any one of a neural network based on a convolution framelet and a neural network including a pooling layer and an unpooling layer.

According to an exemplary embodiment, a quantitative susceptibility mapping image processing method includes receiving a phase image and a magnitude image for reconstructing the quantitative susceptibility mapping image, and reconstructing the quantitative susceptibility mapping image corresponding to the received phase image and the received magnitude image using an unsupervised learning-based neural network generated based on an optimal transport theory, wherein the neural network includes a cycle-consistency generative adversarial network (cycleGAN) structure including at least one generator and at least one discriminator to reconstruct the quantitative susceptibility mapping image.

According to an exemplary embodiment, a quantitative susceptibility mapping image processing apparatus includes a receiver that receives a phase image and a magnitude image for reconstructing the quantitative susceptibility mapping image and a reconstruction unit that reconstructs the quantitative susceptibility mapping image corresponding to the received phase image and the received magnitude image using an unsupervised learning-based neural network, wherein the neural network includes a cycle-consistency generative adversarial network (cycleGAN) structure including at least one generator and at least one discriminator to reconstruct the quantitative susceptibility mapping image.

The neural network may be generated based on an optimal transport theory.

The neural network may be trained using a training dataset containing non-matching data.

The neural network may be subjected to unsupervised learning by using a first neural network that generates a first quantitative susceptibility mapping image corresponding to a first phase image and a first magnitude image after receiving the first phase image and the first magnitude image, a first transform unit that performs Fourier transform on the first quantitative susceptibility mapping image, multiplies the first quantitative susceptibility mapping image by a dipole kernel corresponding to the first phase image and the first magnitude image, and performs inverse Fourier transform on the first quantitative susceptibility mapping image to generate a second phase image, a second transform unit that performs Fourier transform on a second quantitative susceptibility mapping image, which is a ground-truth image, and multiplies the second quantitative susceptibility mapping image by a dipole kernel corresponding to the second quantitative susceptibility mapping image, and performs inverse Fourier transform on the second quantitative susceptibility mapping image to generate a third phase image, a second neural network that generates a third quantitative susceptibility mapping image corresponding to the second phase image and a second magnitude image after receiving the second phase image and the second magnitude image, and a third neural network that discriminates the first quantitative susceptibility mapping image and the second quantitative susceptibility mapping image.

Furthermore, the neural network may be subjected to the unsupervised learning based on a cycle-consistency loss and a gradient difference loss calculated by comparing the first phase image with the second phase image, or the second quantitative susceptibility mapping image with the third quantitative susceptibility mapping image and a total variation loss for the first quantitative susceptibility mapping image, and an adversarial loss between the first quantitative susceptibility mapping image and the second quantitative susceptibility mapping image.

The third neural network may distinguish a quantitative susceptibility mapping image obtained by multiplying the first quantitative susceptibility mapping image by a preset mask and the second quantitative susceptibility mapping image.

The neural network may include any one of a neural network based on a convolution framelet and a neural network including a pooling layer and an unpooling layer.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
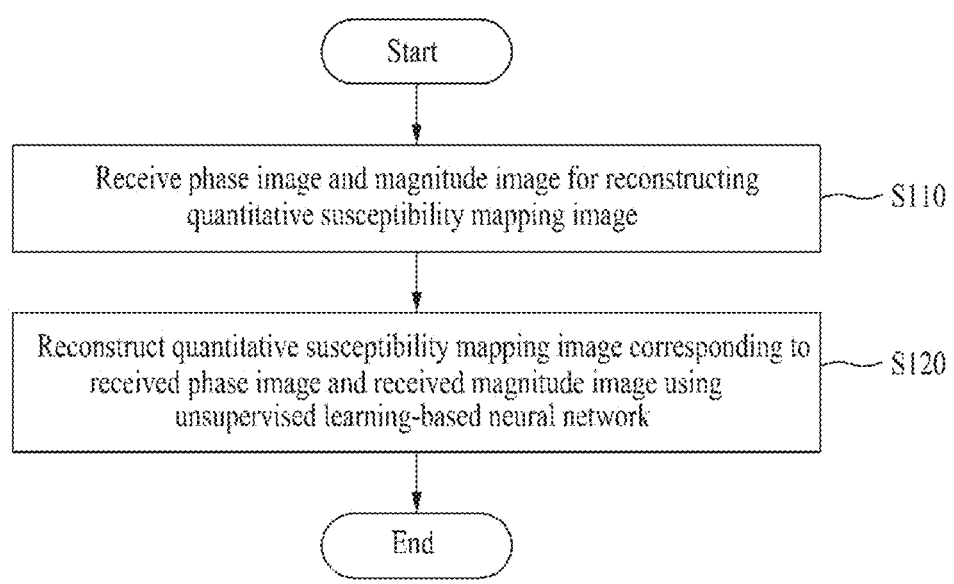
FIG. 1 is a flowchart illustrating an operation of a quantitative susceptibility mapping image processing method according to an embodiment of the inventive concept.

Advantages and features of the inventive concept and methods for achieving them will be apparent with reference to embodiments described below in detail in conjunction with the accompanying drawings. However, the inventive concept is not limited to the embodiments disclosed below, but can be implemented in various forms, and these embodiments are to make the disclosure of the inventive concept complete, and are provided so that this disclosure will be thorough and complete and will fully convey the scope of the invention to those of ordinary skill in the art, which is to be defined only by the scope of the claims.

The terminology used herein is for the purpose of describing particular embodiments only and is not intended to be limiting of the inventive concept. The singular expressions include plural expressions unless the context clearly dictates otherwise. In this specification, the terms "comprises" and/or "comprising" are intended to specify the presence of stated features, integers, steps, operations, elements, parts or combinations thereof, but do not preclude the presence or addition of steps, operations, elements, parts, or combinations thereof.

Unless defined otherwise, all terms (including technical and scientific terms) used herein have the same meanings as commonly understood by one of ordinary skill in the art to which this invention belongs. Further, unless explicitly defined to the contrary, the terms defined in a generally-used dictionary are not ideally or excessively interpreted.

Hereinafter, preferred embodiments of the inventive concept will be described in detail with reference to the accompanying drawings. The same reference numerals are used for the same components in the drawings, and duplicate descriptions of the same components are omitted.

Embodiments of the inventive concept make it a gist of reconstructing a quantitative susceptibility mapping image using an unsupervised learning-based neural network generated by an optimal transport theory.

The neural network used in the inventive concept may include a convolution framelet-based neural network, a neural network including a pooling layer and an unpooling layer, for example, U-Net, as well as various types of neural networks applicable to the inventive concept.

A convolutional framelet refers to a method of representing an input signal through local and non-local bases. In order to reveal the black box characteristics of deep convolutional neural networks, the deep convolutional neural networks are described in detail in a study on a new mathematical theory of deep convolutional framelets (Ye, J C., Han, Y., Cha, E.: Deep convolutional framelets: a general deep learning framework for inverse problems. SIAM Journal on Imaging Sciences 11(2), 991-1048(2018)).

The contribution of the inventive concept is as follows.

Unlike the supervised learning approaches, the method of the inventive concept does not require matched QSM labels for the training so that the trained model is less sensitive to the lack of training data with enough variability and structures. Accordingly, the underestimation issue of QSM values in the supervised learning can be largely overcome.

In contrast to the existing unsupervised learning approaches, the method of the inventive concept learns statistical properties of unpaired QSM labels during training, which makes the training more stable, thus leading to the more accurate QSM map estimation with less outliers.

Unlike the classical approaches and deep image prior (DIP), the method of the inventive concept is a feed-forward neural network that provides instantaneous reconstruction once the cycleGAN training is done, thus making the algorithm very practical.

Prior to describing the inventive concept, conventional technology will be briefly described below.

Various methods have been developed to solve the ill-posed dipole inversion problem. For example, thresholded k-space division (TKD) is a method of filling values near the conical surface of the dipole kernel with a threshold value. Instead of filling the dipole kernel with a specific value, some methods have used additional information for the dipole inversion. Another exemplary method has proposed homogeneity enabled incremental dipole inversion (HEIDI) using homogeneity information from gradient echo phase images. Morphology enabled dipole inversion (MEDI) is a method that exploits the structural consistency between the magnitude image and the reconstructed quantitative susceptibility map. Still another exemplary method has introduced a method based on a sparse linear equation and least squares algorithm (ILSQR) to remove streaking artifacts in reconstructed QSM, and compressed sensing based algorithms were also examined. Annihilating filter-based low-rank Hankel matrix approach (ALOHA) for QSM exploits the sparsity of the data in a certain transform domain to interpolate the missing k-space data in the dipole spectral null. Although above algorithms showed high performance, there are limitations of the above algorithms, such as streaking artifacts, difficulties in optimizing hyper-parameters, and high computational complexity.

To overcome the limitations of traditional methods, QSM reconstruction algorithms based on deep learning have been investigated. Conventional exemplary methods have proposed QSMnet and deepQSM, respectively, which are 3D U-net structures designed for QSM reconstruction. By using of COSMOS images as ground-truth QSM labels, the above methods showed comparable results to those of classical approaches. Another conventional exemplary method has suggested QSMGAN where the adversarial loss was utilized, and still another conventional exemplary method has introduced xQSM where the octave convolutional layers were applied. In addition, still another conventional exemplary method has introduced nonlinear dipole inversion with deep learning using a variational neural network, which combines optimization of nonlinear QSM data model and the data fidelity term.

Although these methods have shown improved image quality compared to conventional methods, the requirement of matched pairs containing phase images and susceptibility maps is a limitation of aforementioned supervised methods. Moreover, one of the biggest issues of supervised learning approach is the generalization error that happens when test data have different characteristics to training data. For example, compared with the conventional QSM, deep learning QSM results may be underestimated the susceptibility values when the susceptibility range in the training data differs from the test data. Moreover, this effect is shown severe when training with synthetic data, which lacks enough variability and structure.

Recently, some deep learning algorithms based on weakly supervised or unsupervised learning were introduced. Conventional exemplary method has proposed weakly supervised learning for QSM reconstruction (wTFI), and wTFI reconstructs QSM without background field removal, and enables the restoration of susceptibility values near the edges of the brain, which can disappear with background field removal. The conventional exemplary method has proposed unsupervised QSM reconstruction method (uQSM) by taking advantage of nonlinear data consistency loss and the total variation loss.

FIG. 1 is a flowchart illustrating an operation of a quantitative susceptibility mapping image processing method according to an embodiment of the inventive concept.

Referring to FIG. 1, a quantitative susceptibility mapping image processing method according to an embodiment of the inventive concept receives a phase image and a magnitude image for reconstructing a quantitative susceptibility mapping image (S110).

When the phase image and the magnitude image are received in step S110, a quantitative susceptibility mapping image corresponding to the received phase image and magnitude image is reconstructed by using a unsupervised learning-based neural network (S120).

Here, the neural network used in the inventive concept may have a cycle Generative Adversarial Network (cycleGAN) structure including at least one generator and at least one discriminator to reconstruct a quantitative susceptibility mapping image.

In addition, the neural network used in the inventive concept may be generated based on an optimal transport theory, and may be learned using a training dataset including non-matching data.

Furthermore, the neural network used in the inventive concept may be subjected to unsupervised learning by using a first neural network (e.g., a generator) that generates a first quantitative susceptibility mapping image corresponding to a first phase image and a first magnitude image after receiving the first phase image and the first magnitude image, a first transform unit that performs Fourier transform on the first quantitative susceptibility mapping image, multiplies the first quantitative susceptibility mapping image by a dipole kernel corresponding to the first phase image and the first magnitude image, and performs inverse Fourier transform on the first quantitative susceptibility mapping image to generate a second phase image, a second transform unit that performs Fourier transform on a second quantitative susceptibility mapping image, which is a ground-truth image, and multiplies the second quantitative susceptibility mapping image by a dipole kernel corresponding to the second quantitative susceptibility mapping image, and performs inverse Fourier transform on the second quantitative susceptibility mapping image to generate a third phase image, a second neural network (e.g., a generator) that generates a third quantitative susceptibility mapping image corresponding to the second phase image and a second magnitude image after receiving the second phase image and the second magnitude image, and a third neural network (e.g., a discriminator) that discriminates the first quantitative susceptibility mapping image and the second quantitative susceptibility mapping image. Here, the first neural network and the second neural network may be the same neural network.

Furthermore, the neural network may be subjected to the unsupervised learning based on a cycle-consistency loss and a gradient difference loss calculated by comparing the first phase image with the second phase image, or the second quantitative susceptibility mapping image with the third quantitative susceptibility mapping image and a total variation loss for the first quantitative susceptibility mapping image, and an adversarial loss between the first quantitative susceptibility mapping image and the second quantitative susceptibility mapping image.

The third neural network may distinguish a quantitative susceptibility mapping image obtained by multiplying the first quantitative susceptibility mapping image by a preset mask and the second quantitative susceptibility mapping image.

The neural network used in the inventive concept may include any one of a neural network based on a convolution framelet and a neural network including a pooling layer and an unpooling layer.

The method of the inventive concept will be described with reference to FIGS. 2 to 5.

Dipole Inversion

When the tissue is brought into the magnetic field, the tissue becomes magnetized. Magnetic susceptibility "X" is the quantitative measure of the degree of magnetization. In MRI, the magnetization of tissues generates the magnetic perturbation along the main magnetic field. This magnetic perturbation, or the phase signal can be represented as [Equation 1]:

$$b(\vec{r})=d(\vec{r})*\chi(\vec{r}), r\in \mathbb{R}^3 \quad \text{[Equation 1]}$$

where b is the phase signal, d is the dipole kernel, and * is the convolution operation. Here, the dipole kernel d is represented by the following Equation:

$$d(\vec{r}) = \frac{1}{4\pi}\frac{3\cos^2\theta - 1}{|\vec{r}|^3}$$

where $\Theta$ is the angle between r and the main magnetic field, whose Fourier domain spectrum is given by [Equation 2]:

$$\hat{d}(\vec{k}) = \frac{1}{3} - \frac{k_z^2}{|\vec{k}|^2} \quad \text{[Equation 2]}$$

where $\vec{k}=[k_x, k_y, k_z]^T$ is a k-space vector.

Accordingly, one of the simplest dipole inversions may be achieved by element-wise division in the Fourier domain, and may be expressed as in [Equation 3] below.

$$\hat{\chi}(\vec{k}) = \frac{\hat{b}(\vec{k})}{\hat{d}(\vec{k})} \quad \text{[Equation 3]}$$

However, [Equation 3] is not stable because $\hat{D}(\vec{k})$ has zero values at the conical surface $$\left(\vec{k}^2 = 3k_z^2\right).$$

Optimal Transport Driven CycleGAN

In the recent mathematical theory of optimal transport driven cycleGAN (OT-cycleGAN), it is revealed that various forms of cycleGAN architecture can be obtained from the dual formulation of an optimal transport problem, in which the transport cost is the sum of the distances in the measurement and image domains. In particular, if the forward mapping is known from the imaging physics as in QSM, the resulting OT-cycleGAN architecture can be significantly simplified. In the inventive concept, the theory is applied for the QSM reconstruction and a measurement model as shown in [Equation 4] below is considered.

$$y=\mathcal{H}x \quad \text{[Equation 4]}$$

where $y\in \mathcal{Y}$ and $x\in \mathcal{X}$ denote the measurement image and the unknown image, respectively, and $\mathcal{H}:\chi \mapsto \mathcal{Y}$ is the known deterministic imaging operator.

In contrast to the supervised learning where the goal is to learn the relationship between the image x and measurement y pairs, there are no matched image-measurement pairs in the unsupervised learning framework. Since sets of images and unpaired measurements can be still acquired, it is a goal to match the probability distributions rather than each individual samples. This can be done by finding transportation maps that transport the probability measures between the two spaces.

Specifically, it is supposed that the target image space $\chi$ is equipped with a probability measure $\mu$, whereas the measurement space $\mathcal{Y}$ is with a probability measure $\nu$. Then, it can be seen that the mass transport from $(\chi, \mu)$ to $(\mathcal{Y}, \nu)$ is performed by the forward operator H, and the mass transportation from the measurement space $(\mathcal{Y}, \nu)$ to the image space ($\chi$, $\mu$) is done by a generator $\Theta$, parameterized by $G_\Theta$: $\mathcal{Y} \mapsto \chi$. Then, the following transportation cost is proposed for the optimal transport problem as shown in the following [Equation 5].

$$c(x,y;\Theta):=\|y-\mathcal{H}\,x\|+\|G_\Theta(y)-x\| \quad \text{[Equation 5]}$$

The [Equation 5] denotes the sum of the distance between a training sample and a transported sample in each space. Rather than minimizing the sample-wise cost using [Equation 5], the goal of the optimal transport is to minimize the average transport cost. More specifically, the optimal transport problem is formulated to find the joint distribution $\pi$ that leads to the minimum average transport cost, which can be expressed as in the following [Equation 6].

$$\inf_{\pi \in \Pi(\mu,v)} \int_{\chi \times \mathcal{Y}} c(x,\,y;\,\Theta) d\pi(x,\,y) \quad \text{[Equation 6]}$$

where $\Pi(\mu, v)$ is the set of joint measures whose marginal distributions in $\chi$ and $\mathcal{Y}$ are $\mu$ and $v$, respectively.

The geometric meaning of the optimal transport using [Equation 5] is explained. More specifically, if the first term in [Equation 5] is only used, the optimal transport is to find the joint probability that minimizes the distance in the empirical distribution $v$ and the so-called "push-forward measure" $v_\mathcal{H}$. Similarly, if the second term in [Equation 5] is only used, the optimal transport problem is to minimize the distance in the empirical distribution $\mu$ and the push-forward measure $\mu_G$. By using both terms in [Equation 5], the optimal transport formulation finds the joint measure that minimizes the sum of the two distances in the measurement and the image spaces.

Using the transportation cost in [Equation 5], the Kantorovich dual formulation is given by [Equation 7] and [Equation 8], $$\min_\Theta \mathbb{K}(\Theta,\,\mathcal{H}) = \min_\Theta \max_\Phi \ell(\Theta;\,\Phi) \quad \text{[Equation 7]}$$

$$\ell(\Theta;\,\Phi) = \gamma\ell_{cycle}(\Theta) + \ell_{WGAN}(\Theta;\,\Phi) \quad \text{[Equation 8]}$$

where $\gamma$ is a suitable hyper-parameter, $I_{cycle}$ is the cycle-consistency loss, $I_{WGAN}$ is the Wasserstein GAN loss. More specifically, $I_{cycle}$ and $I_{WGAN}$ can be expressed by [Equation 9] and [Equation 10].

$$\ell_{cycle}(\Theta) = \int_\chi \|x - G_\Theta(\mathcal{H}\,x)\| d\mu(x) + \int \mathcal{Y} \|y - \mathcal{H}\,G\Theta(y)\| dv(y) \quad \text{[Equation 9]}$$

$$l_{WGAN}(\Theta;\Phi) = \int_\chi \varphi_\phi(x) d\mu(x) - \int \mathcal{Y} \varphi_\phi(G_\Theta(y)) dv(y) \quad \text{[Equation 10]}$$

Since the forward operator $\mathcal{H}$ is assumed known, it is noted that there exists only a single discriminator $\varphi_\phi$, so that there is no need to compete with the forward operator, making the cycleGAN architecture simple.

CycleQSM

In the dipole inversion, a phase image $b \in B$ and a susceptibility map $\chi \in X$ correspond to a noisy measurement and an unobserved image, respectively. Therefore, the forward model of the dipole inversion can be formulated as the following [Equation 11].

$$b = \mathcal{F}^{-1} \hat{d}\, \mathcal{F}\chi \quad \text{[Equation 11]}$$

Where $\mathcal{F}$ and $\mathcal{F}^{-1}$ are 3D Fourier transform and 3D inverse Fourier transform, respectively.

By identifying y:=b, x:=$\chi$ and $\mathcal{H} := \mathcal{F}^{-1}\hat{d}\,\mathcal{F}$, the cycle-consistency loss and the GAN loss can be represented by the following [Equation 12] and [Equation 13].

$$l_{cycle}(\Theta) = \int_\chi \|\chi - G_\Theta(\mathcal{F}^{-1}\hat{d}\,\mathcal{F}\chi)\| d\mu(\chi) + \int_B \|b - \mathcal{F}^{-1}\hat{d}\, \mathcal{F}G_\Theta(b)\| dv(b) \quad \text{[Equation 12]}$$

$$l_{WGAN}(\Theta;\phi) = \int_\chi \varphi_\phi(\chi) d\mu(\chi) - \int_B \varphi_\phi(G_\Theta(b)) dv(b) \quad \text{[Equation 13]}$$

Although these costs can be used directly for the QSM reconstruction, the inventive concept provides additional modifications for a better performance. First, the inventive concept employs the least squares GAN (LSGAN) instead of WGAN loss for faster and more stable training. The link between WGAN and LSGAN was also explained in an existing study (S. Lim, H. Park, S.-E. Lee, S. Chang, B. Sim, and J. C. Ye, "CycleGAN with a blur kernel for deconvolution microscopy: Optimal transport geometry," IEEE Transactions on Computational Imaging, vol. 6, pp. 1127-1138, 2020.) Next, the gradient difference loss ($I_{grad}$) may be added to maintain the edge information, and the gradient difference loss can be expressed as in [Equation 14] below.

$$l_{grad}(\Theta) = \int_\chi \|\nabla\chi - \nabla G_\Theta(\mathcal{F}^{-1}\hat{d}\,\mathcal{F}\chi)\| d\mu(\chi) + \int_B \|\nabla b - \nabla \mathcal{F}^{-1}\hat{d}\,\mathcal{F}G_\Theta(b)\| dv(b) \quad \text{[Equation 14]}$$

where $\nabla$ is a gradient operator for the 3D volume.

To preserve image details and remove noise in reconstructed QSM, the total variation (TV) loss ($l_{TV}$) may be employed and the total variation loss may be expressed in [Equation 15] below.

$$l_{TV}(\Theta) = \int_B \|\nabla G_\Theta(b)\| dv(b) \quad \text{[Equation 15]}$$

Therefore, the final cost function for CycleQSM can be formulated as [Equation 16] below.

$$l(\Theta;\phi) = \gamma l_{cycle}(\Theta) + l_{LSGAN}(\Theta,\phi) + \eta l_{grad}(\Theta) + \mu l_{TV}(\Theta) \quad \text{[Equation 16]}$$

where $\gamma$, $\eta$ and $\rho$ are appropriate hyper-parameters.

It may be noted that the losses in [Equation 14] and [Equation 15] are average values with respect to the marginal distributions. Therefore, the addition of these terms does not change the optimal transport interpretation. In fact, [Equation 16] can be obtained as a dual formulation of the optimal transport problem with the following transportation cost:

$$c_{QSM}(b,\,\chi;\,\Theta) := \|b - \mathcal{F}^{-1}\hat{d}\mathcal{F}\chi\| + \|G_\Theta(b) - \chi\| + \eta(\|\nabla\chi - \nabla G_\Theta(\mathcal{F}^{-1}\hat{d}\mathcal{F}\chi)\| + \|\nabla b - \nabla\mathcal{F}^{-1}\hat{d}\mathcal{F}G_\Theta(b)\|) + \rho\|\nabla G_\Theta(b)\|$$

where $b \in \mathcal{Y}$ and $x \in \chi$ with probability measures $v$ and $\mu$, respectively.

To train and test algorithms, it is possible to use data sets from different sources. First data set is in vivo human brain data that was provided for 2016 QSM challenge. This data set may be acquired from a healthy volunteer by 3T Siemens scanner with 3D gradient echo (GRE) sequence. Acquisition parameters of 2016 QSM challenge data are as follows: resolution=1.06×1.06×1.06 mm$^3$, matrix size=160λ160, TR/TE=25/35 ms. Also, this data set also contains ground-truth QSM which is acquired by COSMOS with 12 different orientation data.

Next, the inventive concept may use in vivo healthy human data from the Cornell MRI Research Lab. This data set may be collected using multi echo GRE sequence with 3T GE system. The acquisition parameters are as follows: Resolution=0.9375×0.9375×1 mm$^3$, matrix size=256λ256λ256, TR/TE$_1$=55/5 ms, and ΔTE=5 ms. QSM is also obtained by COSMOS with 5 different head orientation data.

The third data set was obtained from five healthy volunteers using 3T Siemens system. This data set may be used for ALOHAQSM, and acquired with the following parameters: Resolution=0.75×0.75×1.1 mm$^3$, matrix size=240×320×128, TR/TE$_1$=43/9.35 ms, and ΔTE=8.94 ms.

Last, the inventive concept may have used the data for 2019 QSM challenge. This data set may be obtained through forward simulation based on in vivo human brain data acquired on 7T MR system. The acquisition parameters for 2019 challenge data are as follows: Resolution=0.64×0.64×0.64 mm$^3$, matrix size=164×205, TR/TE$_1$=50/4 ms, and ΔTE=8 ms. The local field data in 2019 challenge data set were simulated with two different contrast levels and two signal-to-noise ratio (SNR) levels, so total four local field maps (Sim1Snr1, Sim1Snr2, Sim2Snr1, Sim2Snr2) may be provided and, in addition, ground-truth QSM data were provided for two different contrast levels.

Table I shows the name and number of volumes of each data set. The 2016 QSM challenge and 2019 QSM challenge data in Table I are used to train our network as well as other deep learning approaches. For unsupervised learning, a matched reference data is not required. Therefore, three local field maps of the ALOHA-QSM data set are also used for training and the remaining two local field maps are used for inference, and furthermore, the Cornell data set is used for the quantitative evaluation of our algorithm.

TABLE 1

|  |  | 2016 QSM Challenge | Cornell | ALOHA-QSM | 2019 QSM Challenge |
|---|---|---|---|---|---|
| Resolution | Voxel pitch (mm$^3$) | 1.06 × 1.06 × 1.06 | 0.9375 × 0.9375 × 1 | 0.75 × 0.75 × 1.1 | 0.64 × 0.64 × 0.64 |
|  | Matrix size | 160 × 160 × 160 | 256 × 256 × 146 | 240 × 320 × 128 | 164 × 205 × 205 |
| No. of Cases | Total | 1 | 1 | 5 | 4 (2 SNR/2 Contrast) |
|  | QSM Ground-truth | 1 (COSMOS) | 1 (COSMOS) | 0 | 2 (Simulation) |
|  | Training | 1 | 0 | 3 | 4 |
|  | Test | 0 | 1 | 2 | 0 |

For data preprocessing, brain mask extraction using the brain extraction tool (BET), multi-coil phase combination by Hermitian inner product (HiP), and multi-echo phase correction by nonlinear frequency map estimation are performed. Laplacian-based phase unwrapping is then applied, and then background phase removal by sophisticated harmonic artifact reduction for phase data with varying spherical kernel is executed. Of course, the data used in the inventive concept is not limited or limited to the data described above, and all data available in the inventive concept may be used.

Network Architectures

Figure 2:
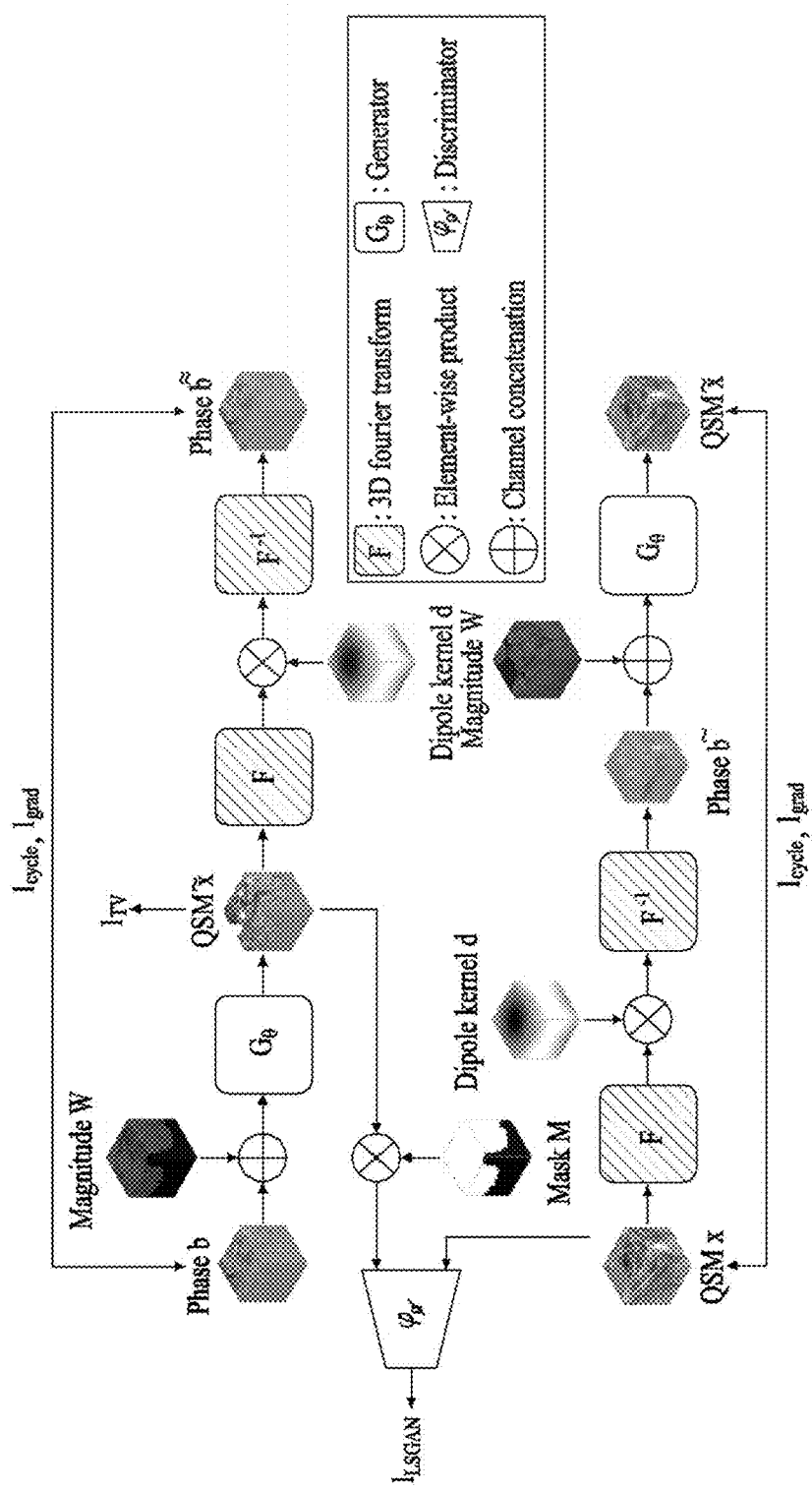
FIG. 2 shows an exemplary diagram for an architecture of cycleQSM of the inventive concept.

FIG. 2 shows an exemplary diagram of the architecture of the cycleQSM of the inventive concept.

Referring to FIG. 2, the forward mapping is described by the deterministic dipole kernel in [Equation 2], cycleQSM has only one pair of the generator and discriminator. That is, unlike the conventional cycleGAN, in the inventive concept, a neural network may have one generator and one discriminator due to the dipole kernel. As a result, the training of the neural network according to the inventive concept may be more stable and faster than the conventional cycleGAN. To provide more information to the generator, the magnitude image is concatenated with the phase image. The dipole kernel for each training step is generated depending on the resolution and direction of the main magnetic field of each data. Accordingly, all the data set in Table 1 with different spatial resolution may be fully utilized for training cycleQSM. Also, the restored (or reconstructed) QSM is multiplied by the brain mask before going through the discriminator. Since, without the brain mask, the discriminator may distinguish real QSM and fake QSM by observing the artifact outside the brain mask region, the inventive concept may stabilize the training process and reduce the artifact outside of the brain region, by multiplying the brain mask.

That is, according to the inventive concept, cycleQSM may be trained through the architecture shown in FIG. 2, and when the training process is completed, only the phase image and the magnitude image may be received using only the actual generator to restore the QSM image.

Specifically, the upper part of cycleQSM shown in FIG. 2 starts with generating a quantitative susceptibility mapping image by inputting the actual phase image to the generator together with the magnitude (or scale) image. In the generated quantitative susceptibility mapping image, the total variation (TV) loss for preserving image details and removing noise may be calculated. Next, the phase image is reconstructed by applying the Fourier transform to the generated quantitative susceptibility mapping image, multiplying the generated dipole kernel according to the resolution, and applying the inverse Fourier transform again. A cycle-consistency loss and a gradient difference loss are calculated by comparing the phase image: reconstructed as described above and a phase image initially used as an input image of the generator. Furthermore, in the lower part of cycleQSM, the phase image is generated using the dipole kernel from the actual quantitative susceptibility mapping image, and then the generator reconstructs the quantitative susceptibility mapping image. Similarly, the cycle-consistency loss and the gradient difference loss are calculated by comparing the reconstructed quantitative susceptibility mapping image with the actual quantitative susceptibility mapping image. Finally, the discriminator may distinguish the actual quantitative susceptibility mapping image from the quantitative susceptibility mapping image generated by the generator. In the learning phase of the generator, the least squares GAN (LSGAN) loss is minimized to deceive the discriminator, while in the learning phase of the discriminator, the least squares adversarial loss is maximized to distinguish the real QSM from the fake QSM. Through this competitive learning, the generator can reconstruct a more realistic quantitative susceptibility mapping image. In addition, the quantitative susceptibility mapping image generated by the generator is multiplied by the brain mask to prevent the discriminator from discriminating between the real QSM and the fake QAM too easily, enabling more stable learning.

Figure 3A:
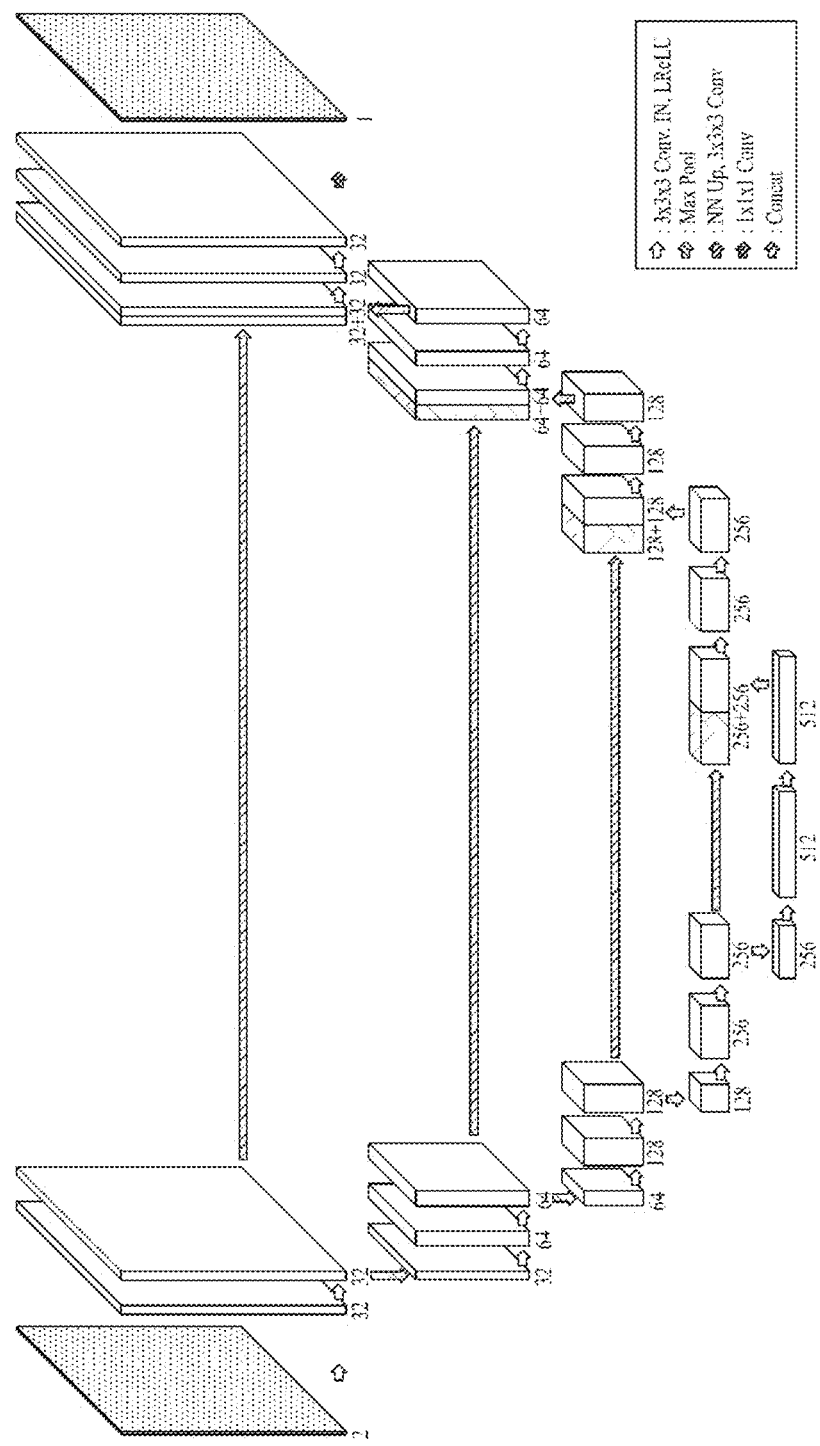
FIG. 3 shows an exemplary diagram for a generator architecture and a discriminator architecture.
Figure 3B:
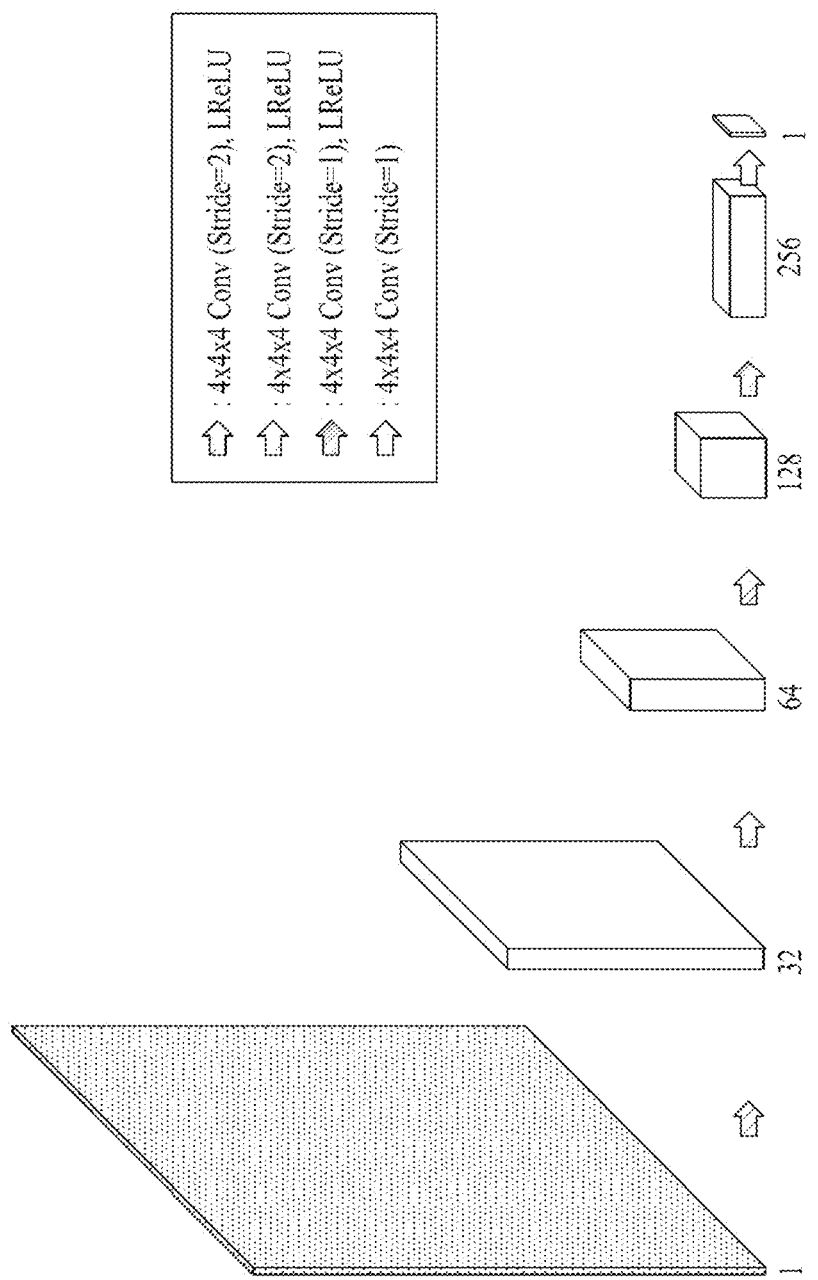

FIG. 3 is a diagram illustrating an example of architecture of a generator and architecture of a discriminator. FIG. 3A shows an architecture of a generator, and FIG. 3B shows an architecture of a discriminator.

As shown in FIG. 3A, the generator may use a 3D U-Net structure based on an U-Net structure. Because of the concatenation of the magnitude image and the phase image, the generator has two input channels. The generator may include 3×3×3 convolution, instance normalization, leaky ReLU, and nearest-neighbor upsampling layers. In addition, the skip connection via channel concatenation is used for the generator. At the end of the network, the final reconstructed QSM is generated through the 1×1×1 convolution.

As shown in FIG. 3B, the discriminator may use patch-GAN discriminator and may consist of 4×4×4 convolution, instance normalization, and leaky ReLU. Inputs of the discriminator are real susceptibility maps or generated susceptibility maps that are multiplied with brain masks.

Since there are only 8 phase images and 3 pieces of QSM label data for network training, the inventive concept may use random patches during training to increase the amount of data. During one epoch, the inventive concept may extract a total of 3000 phase and unpaired QSM random patches of size 64×64×64, respectively. In the inference step, a phase volume is cropped into patches of size 64×64 with a stride of 16×16×16, and all patch inference results are combined to reconstruct the entire QSM volume. Moreover, the inventive concept may apply data augmentation by flipping with respect to each axis, and rotating in a plane perpendicular to the direction of the main magnetic field.

The inventive concept may use Adam optimizer with β1=0.5, β2=0.999, and learning rate of 0.00001 and also, choose γ=10, η=1, and ρ=0.1 for [Equation 16]. In the inventive concept, the cycleGAN is trained for 50 epochs, and implemented in Python by TensorFlow.

The method of the inventive concept may be compared with several conventional methods to verify the performance of the algorithm. First, TKD is used to replace the values in the conical surfaces of the dipole kernel with a certain threshold value, and may be expressed as in [Equation 17] below.

$$\hat{d}(\vec{k};a) = \begin{cases} d(\vec{k}) & |d(\vec{k})| > a \\ a \cdot \text{sign}(d(\vec{k})) & |d(\vec{k})| \le a \end{cases} \quad \text{[Equation 17]}$$

where α is a threshold value.

Next, MEDI is also compared with our algorithm and the QSM reconstruction by MEDI can be formulated as in [Equation 18] below.

$$\min_{\chi} \|W(b - \mathcal{F}^{-1}d\mathcal{F}\chi)\|_2^2 + \lambda\|M\nabla\chi\|_1 \quad \text{[Equation 18]}$$

where W is the structural weight matrix which is derived by the magnitude image, and M is the binary mask that contains the edge information of the magnitude image.

In addition, the inventive concept may compare cycleQSM with iLSQR and ALOHA-QSM and in our comparison experiments, the inventive concept may use a=0.1 for TKD, λ=600 for MEDI, and 30 iteration steps for iLSQR, respectively. Also, hyper-parameters for ALOHA-QSM are set to $\lambda=10^{1.5}$, $\mu=10^{-1.5}$ for Cornell data, and $\lambda=10^{2.4}$, $\mu=10^{-2.2}$ for ALOHA-QSM data, respectively.

The method according to the inventive concept may be also compared with other deep learning methods. Supervised learning using the same U-Net network is compared with the method according to the inventive concept. The network in supervised learning may be trained using L1 loss during 50 epochs with the learning rate of 0.0001. Next, deep image prior (DIP) is used for dipole inversion and is optimized for each volume without training, and the optimization in DIP can be formulated as in [Equation 19] below.

$$\min_{\chi} \|W(e^{j\mathcal{F}^{-1}d\mathcal{F}\chi} - e^{jb})\|_1 + \lambda\|\nabla\chi\|_1 \quad \text{[Equation 19]}$$

where W is a noise weighting factor that is obtained from the magnitude image.

The inventive concept may use λ in [Equation 19] as 0.001 for the best performance. The network architecture in DIP is same as the generator according to the inventive concept, but the number of channels may be reduced by half due to the GPU memory limitation. In addition, uQSM may be used for comparison as another unsupervised learning method. uQSM may minimize the loss in [Equation 19] with λ=0:001, but it is trained with training data first, then the trained network is used for the reconstruction of test data. uQSM may be trained during 50 epochs with the learning rate of 0.0001.

To evaluate algorithms, the peak signal-to-noise ratio (PSNR) and the structural similarity index metrics (SSIM) may be used as quantitative metrics. PSNR and SSIM may be measured for 3D volume of Cornell data which has ground-truth QSM. Also, the root mean square error (RMSE) which is calculated as in [Equation 20] below may be used.

$$RMSE = \sqrt{\frac{\sum_{i=1}^{N}(\chi_i - \tilde{\chi}_i)^2}{N}} \quad \text{[Equation 20]}$$

where N is the number of pixels which in the brain mask, and $\chi_i$ and $\tilde{\chi}_i$ are pixel intensities of ground-truth and reconstructed QSM.

Figure 4:
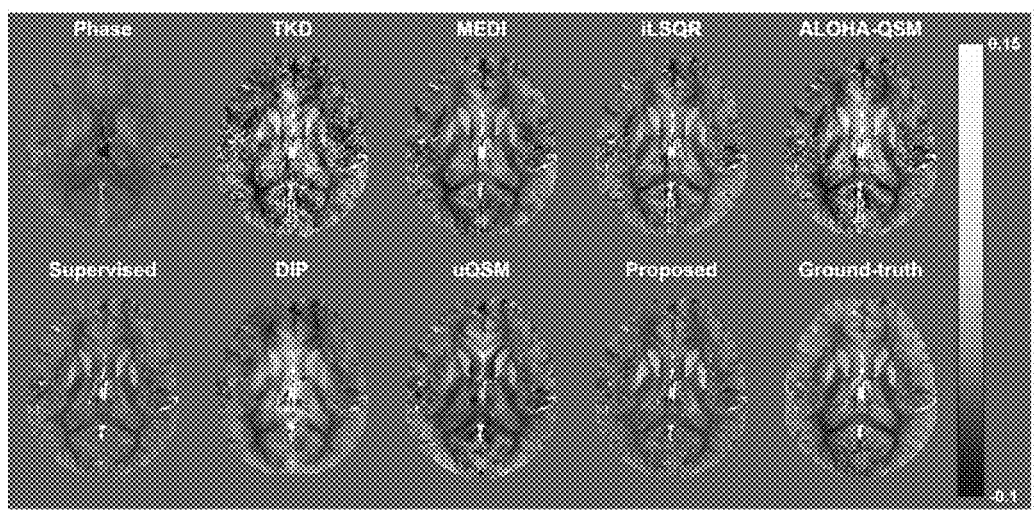
FIG. 4 is a diagram illustrating an example of a result of reconstructing a quantitative susceptibility mapping image using a method of the inventive concept and various conventional methods.

FIG. 4 shows an exemplary view of results of reconstructing a susceptibility mapping image using the method of the inventive concept and various existing methods, and in FIG. 4, phase represents a phase image, TKD, MEDI, iLSQR, and ALOHA-QSM represent QSMs reconstructed by conventional QSM reconstruction methods, supervised represents a QSM reconstructed by a supervised learning-based deep-learning method, DIP and uQSM represent QSMs reconstructed by unsupervised learning-based deep learning methods, proposed represents QSM reconstructed by the method of the inventive concept, and ground-truth represents the ground-truth QSM.

As can be seen from FIG. 4, it can be seen that the QSM reconstructed from TKD has severe streaking artifacts, and the QSM reconstructed by MEDI does not have streaking artifacts, but provides an excessively smooth reconstruction result. Furthermore, the QSMs reconstructed by iLSQR and ALOHA-QSM are more realistic QSMs, but it can be seen that streaking artifacts remain in the reconstructed QSM,s and supervised learning reconstructs QSM close to the ground-truth QSM without streaking artifacts. The output of DIP is smoothed and some susceptibility values are not restored. Also, DIP requires very long reconstruction time compared to other methods because it has to be optimized to each volume. uQSM can reconstruct QSM without label data, but uQSM generates excessively-smoothed output so that some of structures in the reconstructed QSM are not recognizable. On the other hand, the method according to the inventive concept reconstructs QSM that are close to the ground-truth data without the artifacts. In addition, the method according to the inventive concept requires similar reconstruction time as supervised learning.

Figure 5A:
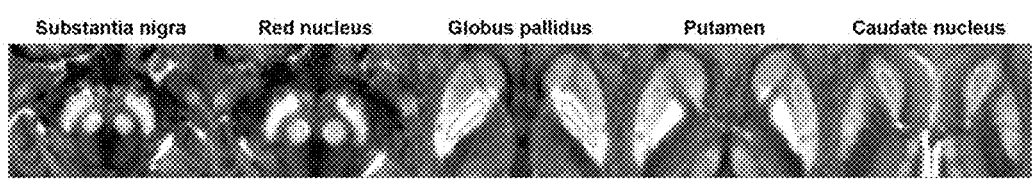
FIG. 5 is a diagram illustrating an example for describing an analysis result using susceptibility values of a ground-truth image and susceptibility values of an image reconstructed by various reconstruction methods.
Figure 5B:
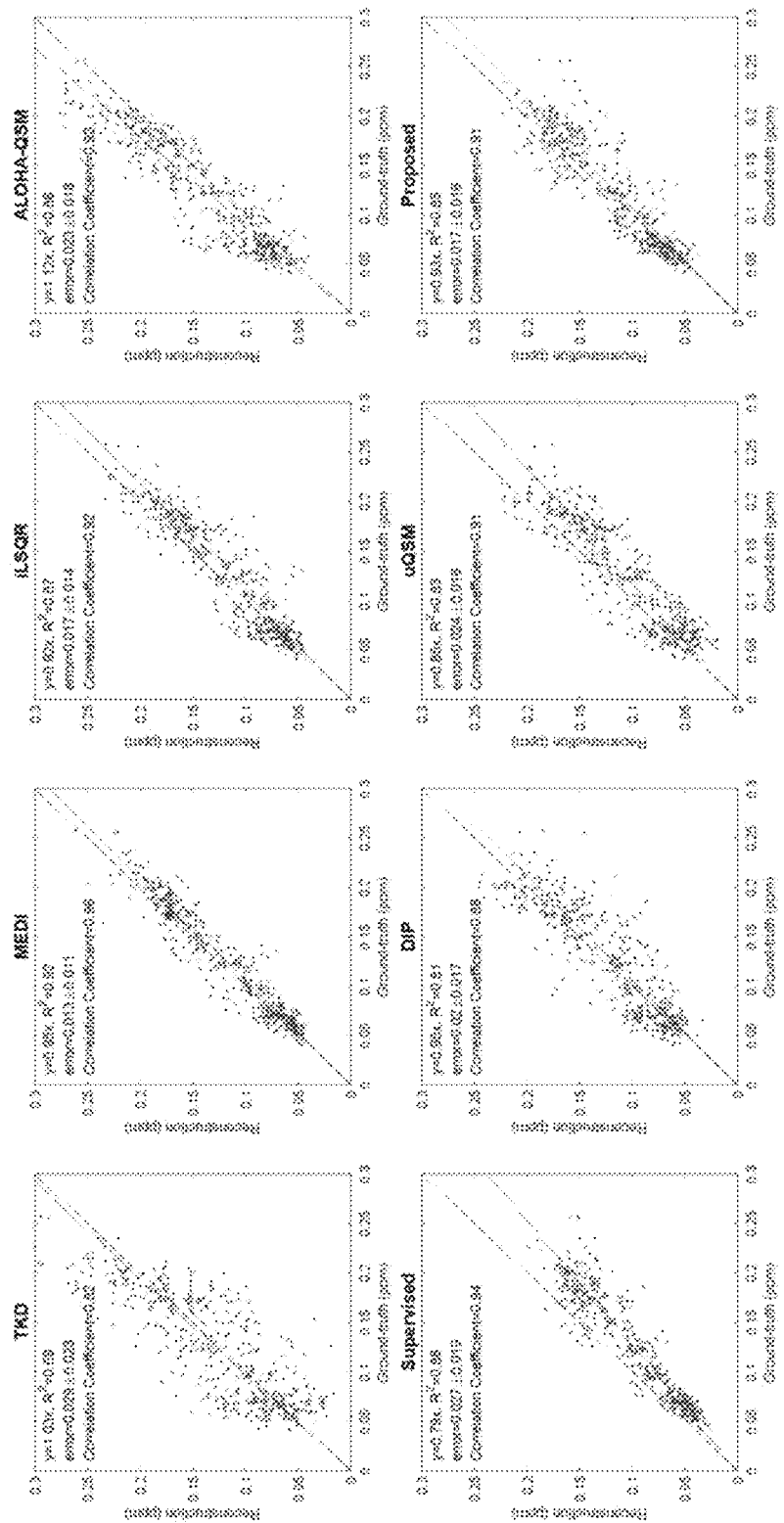

FIG. 5 is an exemplary view for explaining an analysis result using the susceptibility values of the ground-truth image and the susceptibility values of images reconstructed by various reconstruction methods. FIG. 5A shows each brain structure, and FIG. 5B shows results of linear regression analysis on the susceptibility values of the ground-truth image and the susceptibility values of images reconstructed by various reconstruction methods. Here, in FIG. 5B, the horizontal axis represents the susceptibility values of the ground-truth image, the vertical axis represents the susceptibility values of the reconstructed image, and the susceptibility values may be extracted from the gray matter structures of FIG. 5A.

As can be seen from FIG. 5, the deep learning-based methods different from the conventional methods show many error values, underestimation, overestimation, or the like, whereas the method of the inventive concept shows small errors and accurate linear regression results.

As described above, the method according to an embodiment of the inventive concept may reconstruct a quantitative susceptibility mapping image using an unsupervised learning-based neural network generated by the optimal transport theory.

In addition, the inventive concept provides a specific contrast image through a quantitative susceptibility mapping image or provides information that is sensitive to biomarkers such as iron deposition and helpful in diagnosing diseases, and thus, is applicable to all fields using quantitative susceptibility mapping images, medical equipment, or the like.

Figure 6:
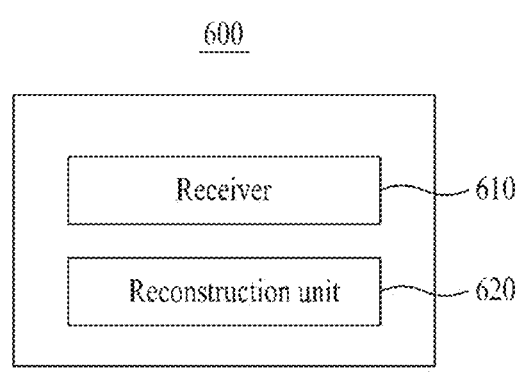
FIG. 6 is a diagram illustrating a configuration of a quantitative susceptibility mapping image processing apparatus according to an embodiment of the inventive concept.

FIG. 6 illustrates a configuration of a quantitative susceptibility mapping image processing apparatus according to an embodiment of the inventive concept, and illustrates a conceptual configuration of an apparatus for performing the methods of FIGS. 1 to 5.

Referring to FIG. 6, a quantitative susceptibility mapping image processing apparatus 600 according to an embodiment of the inventive concept includes a receiver 610 and a reconstruction unit 620.

The receiver 610 receives a phase image and a magnitude image for reconstructing a quantitative susceptibility mapping image.

The reconstruction unit 620 reconstructs a quantitative susceptibility mapping image corresponding to the received phase image and magnitude image by using an unsupervised learning-based neural network.

Here, the neural network used in the inventive concept may have a cycle Generative Adversarial Network (cycle-GAN) structure including at least one: generator and at least one discriminator to reconstruct a quantitative susceptibility mapping image.

In addition, the neural network used in the inventive concept may be generated based on the optimal transport theory, and may be learned using a training dataset including non-matching data.

Furthermore, the neural network used in the inventive concept may be subjected to unsupervised learning by using a first neural network (e.g., a generator) that generates a first quantitative susceptibility mapping image corresponding to a first phase image and a first magnitude image after receiving the first phase image and the first magnitude image, a first transform unit that performs Fourier transform on the first quantitative susceptibility mapping image, multiplies the first quantitative susceptibility mapping image by a dipole kernel corresponding to the first phase image and the first magnitude image, and performs inverse Fourier transform on the first quantitative susceptibility mapping image to generate a second phase image, a second transform unit that performs Fourier transform on a second quantitative susceptibility mapping image, which is a ground-truth image, and multiplies the second quantitative susceptibility mapping image by a dipole kernel corresponding to the second quantitative susceptibility mapping image, and performs inverse Fourier transform on the second quantitative susceptibility mapping image to generate a third phase image, a second neural network (e.g., a generator) that generates a third quantitative susceptibility mapping image corresponding to the second phase image and a second magnitude image after receiving the second phase image and the second magnitude image, and a third neural network (e.g., a discriminator) that discriminates the first quantitative susceptibility mapping image and the second quantitative susceptibility mapping image. Here, the first neural network and the second neural network may be the same neural network. Here, the first neural network and the second neural network may be the same neural network.

Furthermore, the neural network may be subjected to unsupervised learning based on a cycle-consistency loss and a gradient difference loss calculated by comparing the first phase image with the second phase image, or the second quantitative susceptibility mapping image with the third quantitative susceptibility mapping image and a total variation loss for the first quantitative susceptibility mapping image, and an adversarial loss between the first quantitative susceptibility mapping image and the second quantitative susceptibility mapping image.

The third neural network may distinguish a quantitative susceptibility mapping image obtained by multiplying the first quantitative susceptibility mapping image by a preset mask and the second quantitative susceptibility mapping image.

The neural network used in the inventive concept may include any one of a neural network based on a convolution framelet and a neural network including a pooling layer and an unpooling layer.

Although the description is omitted with reference to the apparatus of FIG. 6, components constituting FIG. 6 may include all the contents described with reference to FIGS. 1 to 5, which are obvious to those skilled in the art.

The apparatus described herein may be implemented with hardware components and software components and/or a combination of the hardware components and the software components. For example, the apparatus and components described in the embodiments may be implemented using one or more general-purpose or special purpose computers, such as, for example, a processor, a controller and an arithmetic logic unit (ALU), a digital signal processor, a microcomputer, a field programmable array (FPA), a programmable logic unit (PLU), a microprocessor or any other device capable of executing and responding to instructions. The processing device may run an operating system (OS) and one or more software applications that run on the OS. The processing device also may access, store, manipulate, process, and create data in response to execution of the software. For convenience of understanding, one processing device is described as being used, but those skilled in the art will appreciate that the processing device includes a plurality of processing elements and/or multiple types of processing elements. For example, the processing device may include multiple processors or a single processor and a single controller. In addition, different processing configurations are possible, such a parallel processors.

The software may include a computer program, a piece of code, an instruction, or some combination thereof, for independently or collectively instructing or configuring the processing device to operate as desired. Software and/or data may be embodied in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more computer readable recording mediums.

The above-described methods may be embodied in the form of program instructions that can be executed by various computer means and recorded on a computer-readable medium. The computer readable medium may include program instructions, data files, data structures, and the like, alone or in combination. Program instructions recorded on the media may be those specially designed and constructed for the purposes of the inventive concept, or they may be of the kind well-known and available to those having skill in the computer software arts. Examples of computer readable recording media include magnetic media such as hard disks, floppy disks and magnetic tape, optical media such as CD-ROMs, DVDs, and magnetic disks such as floppy disks, Magneto-optical media, and hardware devices specifically configured to store and execute program instructions, such as ROM, RAM, flash memory, and the like. Examples of program instructions include not only machine code generated by a compiler, but also high-level language code that can be executed by a computer using an interpreter or the like.

Although the embodiments have been described by the limited embodiments and the drawings as described above, various modifications and variations are possible to those skilled in the art from the above description. For example, the described techniques may be performed in a different order than the described method, and/or components of the described systems, structures, devices, circuits, etc. may be combined or combined in a different form than the described method, or other components, or even when replaced or substituted by equivalents, an appropriate result can be achieved.

Therefore, other implementations, other embodiments, and equivalents to the claims are within the scope of the following claims.

According to the embodiments of the inventive concept, it is possible to reconstruct a quantitative susceptibility mapping image using an unsupervised learning-based neural network.

Furthermore, since the quantitative susceptibility mapping image provides specific image contrast unlike magnetic resonance imaging (MRI) or provides information that is sensitive to biomarkers such as iron deposition and helpful in diagnosing diseases, the inventive concept is applicable to all fields using quantitative susceptibility mapping images, medical equipment, or the like.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A quantitative susceptibility mapping image processing method for reconstructing a quantitative susceptibility mapping (QSM) image, the method comprising:
   receiving a phase image and a magnitude image for reconstructing the quantitative susceptibility mapping image; and
   reconstructing the quantitative susceptibility mapping image corresponding to the received phase image and the received magnitude image using an unsupervised learning-based neural network,
   wherein the unsupervised learning-based neural network includes a cycle-consistency generative adversarial network (cycleGAN) structure including at least one generator and at least one discriminator to reconstruct the quantitative susceptibility mapping image, and
   wherein the unsupervised learning-based neural network is trained by unsupervised learning by using:
   a first neural network configured to generate a first quantitative susceptibility mapping image corresponding to a first phase image and a first magnitude image after receiving the first phase image and the first magnitude image;
   a first transform unit configured to perform Fourier transform on the first quantitative susceptibility mapping image, multiply the first quantitative susceptibility mapping image by a dipole kernel corresponding to the first phase image and the first magnitude image, and perform inverse Fourier transform on the first quantitative susceptibility mapping image to generate a second phase image;
   a second transform unit configured to perform Fourier transform on a second quantitative susceptibility mapping image, which is a ground-truth image, and multiply the second quantitative susceptibility mapping image by a dipole kernel corresponding to the second quantitative susceptibility mapping image, and perform inverse Fourier transform on the second quantitative susceptibility mapping image to generate a third phase image;
   a second neural network configured to generate a third quantitative susceptibility mapping image corresponding to the second phase image and a second magnitude image after receiving the second phase image and the second magnitude image; and a third neural network configured to discriminate the first quantitative susceptibility mapping image and the second quantitative susceptibility mapping image.

2. The quantitative susceptibility mapping image processing method of claim 1, wherein the neural network is generated based on an optimal transport theory.

3. The quantitative susceptibility mapping image processing method of claim 1, wherein the neural network is trained using a training dataset containing non-matching data.

4. The quantitative susceptibility mapping image processing method of claim 1, wherein the neural network is trained by the unsupervised learning based on a cycle-consistency loss and a gradient difference loss calculated by comparing the first phase image with the second phase image, or the second quantitative susceptibility mapping image with the third quantitative susceptibility mapping image and a total variation loss for the first quantitative susceptibility mapping image, and an adversarial loss between the first quantitative susceptibility mapping image and the second quantitative susceptibility mapping image.

5. The quantitative susceptibility mapping image processing method of claim 1, wherein the third neural network distinguishes a quantitative susceptibility mapping image obtained by multiplying the first quantitative susceptibility mapping image by a preset mask and the second quantitative susceptibility mapping image.

6. The quantitative susceptibility mapping image processing method of claim 1, wherein the neural network includes any one of a neural network based on a convolution framelet and a neural network including a pooling layer and an unpooling layer.

7. A quantitative susceptibility mapping image processing apparatus for reconstructing a quantitative susceptibility mapping (QSM) image, the apparatus comprising:
  receiving a phase image and a magnitude image for reconstructing the quantitative susceptibility mapping image; and
  reconstructing the quantitative susceptibility mapping image corresponding to the received phase image and the received magnitude image using an unsupervised learning-based neural network,
  wherein the unsupervised learning-based neural network includes a cycle-consistency generative adversarial network (cycleGAN) structure including at least one generator and at least one discriminator to reconstruct the quantitative susceptibility mapping image, and
  wherein the unsupervised learning-based neural network is trained by unsupervised learning by using:
  a first neural network configured to generate a first quantitative susceptibility mapping image corresponding to a first phase image and a first magnitude image after receiving the first phase image and the first magnitude image;
  a first transform unit configured to perform Fourier transform on the first quantitative susceptibility mapping image, multiply the first quantitative susceptibility mapping image by a dipole kernel corresponding to the first phase image and the first magnitude image, and perform inverse Fourier transform on the first quantitative susceptibility mapping image to generate a second phase image;
  a second transform unit configured to perform Fourier transform on a second quantitative susceptibility mapping image, which is a ground-truth image, and multiply the second quantitative susceptibility mapping image by a dipole kernel corresponding to the second quantitative susceptibility mapping image, and perform inverse Fourier transform on the second quantitative susceptibility mapping image to generate a third phase image;
  a second neural network configured to generate a third quantitative susceptibility mapping image corresponding to the second phase image and a second magnitude image after receiving the second phase image and the second magnitude image; and
  a third neural network configured to discriminate the first quantitative susceptibility mapping image and the second quantitative susceptibility mapping image.

8. The quantitative susceptibility mapping image processing apparatus of claim 7, wherein the neural network is generated based on an optimal transport theory.

9. The quantitative susceptibility mapping image processing apparatus of claim 7, wherein the neural network is trained using a training dataset containing non-matching data.

10. The quantitative susceptibility mapping image processing apparatus of claim 7, wherein the neural network is trained by the unsupervised learning based on a cycle-consistency loss and a gradient difference loss calculated by comparing the first phase image with the second phase image, or the second quantitative susceptibility mapping image with the third quantitative susceptibility mapping image and a total variation loss for the first quantitative susceptibility mapping image, and an adversarial loss between the first quantitative susceptibility mapping image and the second quantitative susceptibility mapping image.

11. The quantitative susceptibility mapping image processing apparatus of claim 7, wherein the third neural network distinguishes a quantitative susceptibility mapping image obtained by multiplying the first quantitative susceptibility mapping image by a preset mask and the second quantitative susceptibility mapping image.

12. The quantitative susceptibility mapping image processing apparatus of claim 7, wherein the neural network includes any one of a neural network based on a convolution framelet and a neural network including a pooling layer and an unpooling layer.

* * * * *